United States Patent
Lee et al.

(10) Patent No.: US 12,280,135 B2
(45) Date of Patent: Apr. 22, 2025

(54) COSMETIC COMPOSITION FOR PEEL-OFF-TYPE PACKS, AND METHOD FOR PRODUCING SAME

(71) Applicant: KOLMAR KOREA CO., LTD., Sejong-si (KR)

(72) Inventors: Jeong Mi Lee, Sejong-si (KR); Sang Keun Han, Chungcheongnam-do (KR); Hyeong Choi, Sejong-si (KR); Sung Won Lee, Daejeon (KR)

(73) Assignee: KOLMAR KOREA CO., LTD., Sejong-si (KR)

( * ) Notice: Subject to any disclaimer, the term of this patent is extended or adjusted under 35 U.S.C. 154(b) by 51 days.

(21) Appl. No.: 17/939,569

(22) Filed: Sep. 7, 2022

(65) Prior Publication Data
US 2022/0409513 A1    Dec. 29, 2022

Related U.S. Application Data

(62) Division of application No. 16/064,104, filed as application No. PCT/KR2016/013945 on Nov. 30, 2016, now abandoned.

(30) Foreign Application Priority Data

Jan. 5, 2016  (KR) .......................... 10-2016-0001150

(51) Int. Cl.
| | |
|---|---|
| *A61K 8/81* | (2006.01) |
| *A61K 8/02* | (2006.01) |
| *A61K 8/19* | (2006.01) |
| *A61K 8/25* | (2006.01) |
| *A61K 8/26* | (2006.01) |
| *A61K 8/29* | (2006.01) |

(Continued)

(52) U.S. Cl.
CPC .......... *A61K 8/8129* (2013.01); *A61K 8/0212* (2013.01); *A61K 8/022* (2013.01); *A61K 8/19* (2013.01); *A61K 8/25* (2013.01); *A61K 8/26* (2013.01); *A61K 8/29* (2013.01); *A61K 8/34* (2013.01); *A61K 8/731* (2013.01); *A61K 8/8147* (2013.01); *A61K 8/8176* (2013.01); *A61K 8/891* (2013.01); *A61Q 19/00* (2013.01)

(58) Field of Classification Search
CPC .... A61K 8/8129; A61K 8/0212; A61K 8/022; A61K 8/25; A61K 8/34; A61K 8/731; A61K 8/8147; A61K 8/8176
See application file for complete search history.

(56) References Cited

U.S. PATENT DOCUMENTS

| | | | | |
|---|---|---|---|---|
| 6,503,232 | B1 * | 1/2003 | Kawai | ................... A61F 13/126 |
| | | | | 604/289 |
| 2018/0303744 | A1 * | 10/2018 | Dörr | ........................ A61Q 1/04 |

OTHER PUBLICATIONS

Tong Yang; "Cosmetic Pharmacology"; China Medical Science and Technology Press; 2007: 321-322, English translation (Year: 2007).*

* cited by examiner

*Primary Examiner* — Timothy P Thomas
(74) *Attorney, Agent, or Firm* — The PL Law Group, PLLC (57) ABSTRACT

A cosmetic composition for peel-off-type packs includes a thickener so that pearl or powder particles are stabilized in a formulation to thus impart a sophisticated and differentiated appearance. The content of an alcohol ingredient therein is controlled to accelerate drying, which maximizes a lifting effect. Silicone, imparting a feeling of conditioning, is introduced into polyvinyl alcohol and polyvinyl pyrrolidone, which are film formers, thus minimizing skin irritation upon peeling off.

2 Claims, 2 Drawing Sheets (51) Int. Cl.
*A61K 8/34* (2006.01)
*A61K 8/73* (2006.01)
*A61K 8/891* (2006.01)
*A61Q 19/00* (2006.01)

FIG.1

FIG.2A p<0.05 by Wilcoxon Signed rank test
Change ratio(%)=(after-before)/before*100

FIG. 2B

COSMETIC COMPOSITION FOR PEEL-OFF-TYPE PACKS, AND METHOD FOR PRODUCING SAME

CROSS REFERENCE TO RELATED APPLICATIONS AND CLAIM OF PRIORITY

This application is a divisional application of Application Ser. No. 16/064,104, filed on Jun. 20, 2018, which is a National Stage entry from International Application No. PCT/KR2016/013945, filed Nov. 30, 2016, which claims priority to the benefit of Korean Patent Application No. 10-2016-0001150 filed in the Korean Intellectual Property Office on Jan. 5, 2016, the entire contents of which are incorporated herein by reference.

BACKGROUND

1. Technical Field

The present invention relates to a cosmetic composition for peel-off-type packs and the manufacture of the same. More particularly, the present invention relates to a cosmetic composition for peel-off-type packs, which includes a thickener so that pearl or powder particles are stabilized in a formulation to thus impart a sophisticated and differentiated appearance, and a method of manufacturing the same. The content of an alcohol ingredient therein is controlled to accelerate drying, which maximizes a lifting effect. Silicone, imparting a feeling of conditioning, is introduced into polyvinyl alcohol and polyvinyl pyrrolidone, which are film formers, thus minimizing skin irritation upon peeling off.

2. Background Art

The skin, surrounding the entire human body, plays an important role in protecting the human body from environmental factors such as various external irritants or pollutants, and is broadly divided into the epidermis, dermis, and subcutaneous tissues. The outermost layer of the epidermis is the stratum corneum, which comes into direct contact with cosmetics and which is the part showing the aesthetic state of the skin. Through the process of keratinization of epidermal cells, keratinocytes in the outermost layer are repeatedly released and formed, and millions of dead keratinocytes are released from the skin and replaced by new keratinocytes every day.

When abnormal keratinocytes are formed due to an abnormal keratinization process or when keratinocytes are unfavorably released, the skin appears grayish, applied makeup does not appear as desired, or the skin does not appear vigorous. In this case, people use various pack products so as to give sufficient nutrition and moisturizing to the epidermal layer of the skin, thus favorably releasing the stratum corneum.

Pack products include various formulations such as a cream type, a gel type, a powder type, and a mask type, and are broadly classified into a peel-off type, a wash-off type, and a leave-on type depending on the manner of usage.

Of these, in the case of the peel-off-type product, after a liquid- or gel-type product is applied to the skin, the nutrients in the pack are absorbed into the skin and the product applied on the surface of the skin is dried over time to thus form a film. The film is readily peeled off without washing with water, and is thus convenient. Particularly, since sebum or various kinds of waste materials in the keratinized stratum corneum and pores are adsorbed on the dried film and thus removed when the film is peeled off, the peel-off-type product may provide the effects of nutrition supply and immediate waste removal.

In Korean Patent No. 0163511, in order to provide a cosmetic composition for packs which is excellent in stability and keratin removal effect, fast in drying speed, and remarkably low in skin irritation, polyvinyl alcohol and polyvinyl pyrrolidone are used as a film-forming agent, white particulate materials such as titanium dioxide, kaolin, and talc are used, and a clay thickener including magnesium aluminum silicate is used as a clay mineral. Korean Laid-Open Patent No. 1242969 discloses a cosmetic composition for peel-off-type packs, which includes a first agent containing sodium alginate and a second agent containing a film-curing agent in order to increase a drying speed and to reduce skin irritation in the peel-off-type pack including polyvinyl alcohol as a base. The first agent is an emulsified type and is an emulsified composition that is constituted by an oil-phase composition including an emulsifying agent and an oil-based emollient agent and a water-phase composition including an aqueous solvent, a humectant, and an aqueous emollient agent. The first agent and a non-emulsified-type second agent including sodium alginate are used step by step, thus providing a moisturizing effect to the skin.

However, the peel-off-type pack formulations of the above-mentioned registered patents have difficulty in stabilizing particles such as pearl and/or solid powder. Further, there is a problem in that, due to the formation of a strong film of polyvinyl alcohol, which is a main ingredient for forming the film, they may cause skin irritation even though they are useful in removing waste materials. Conventionally, polyol is used in order to reduce skin irritation upon peeling off. However, the polyol is not absorbed well on the skin and is difficult to volatilize. Therefore, the drying time is lengthened, making usage difficult. Accordingly, a pack-off-type pack formulation based only on polyvinyl alcohol may have restrictions on the use of a humectant such as polyol, and other emollients are not easy to use.

SUMMARY

Accordingly, the present invention has been made keeping in mind the above problems occurring in the prior art, and an object of the present invention is to provide a cosmetic composition for peel-off-type packs, in which pearl or powder particles do not agglomerate in a formulation and which imparts a sophisticated and differentiated appearance. The cosmetic composition is rapidly dried to thus maximize a lifting effect, and silicone, imparting a feeling of conditioning, is introduced into polyvinyl alcohol and polyvinyl pyrrolidone, which are film formers, thus minimizing skin irritation upon peeling off.

Another object of the present invention is to provide a method of manufacturing a cosmetic composition for peel-off-type packs, in which two kinds of thickeners are used and alcohol and silicone are added to polyvinyl alcohol and polyvinyl pyrrolidone, which are film formers, in order to manufacture a peel-off-type pack that realizes rapid drying, no irritation upon peeling off, and a maximized lifting effect.

In order to accomplish the above object of the present invention, the present invention provides a cosmetic composition for peel-off-type packs, which includes pearl or powder particles, a first thickener, a second thickener, and a film former.

In an embodiment of the present invention, the cosmetic composition may further include alcohol and silicone.

The film former may include polyvinyl alcohol, polyvinyl pyrrolidone, and a combination thereof.

The first thickener may include a material selected from the group consisting of gum arabic, carrageenan, galactan, agar, guar gum, pectin, mannan, wheat starch, rice starch, corn starch, potato starch, xanthan gum, albumin, collagen, gelatin, ethyl cellulose, carboxymethyl cellulose, carboxymethyl ethyl cellulose, crystalline cellulose, hydroxyethyl cellulose, hydroxymethyl cellulose, methyl hydroxypropyl cellulose, carboxyvinyl polymers, sodium polyacrylate, polyvinyl alcohol, and acrylate/alkyl acrylate crosspolymers.

The second thickener may include a material selected from the group consisting of gum arabic, carrageenan, galactan, agar, guar gum, pectin, mannan, wheat starch, rice starch, corn starch, potato starch, xanthan gum, albumin, collagen, gelatin, ethyl cellulose, carboxymethyl cellulose, carboxymethyl ethyl cellulose, crystalline cellulose, hydroxyethyl cellulose, hydroxymethyl cellulose, methyl hydroxypropyl cellulose, carboxyvinyl polymers, sodium polyacrylate, polyvinyl alcohol, and acrylate/alkyl acrylate crosspolymers.

The silicone may include one or more selected from the group consisting of decamethylcyclopentasiloxane, dimethicone, methyl polysiloxane, pentasiloxane, hexasiloxane, and phenyl dimethicone.

In order to accomplish the other object of the present invention, the present invention provides a method of manufacturing a cosmetic composition for peel-off-type packs. The method includes (1) manufacturing a homogenized water-phase part by mixing about 0.1 to about 0.5 parts by weight of a first thickener with purified water, followed by heating to about 70 to about 90° C. and then dispersion; (2) manufacturing a primarily homogenized film-former phase by mixing about 5 to about 20 parts by weight of polyvinyl alcohol with the homogenized water-phase part, followed by heating to about 70 to about 90° C.; (3) manufacturing a homogenized thickener phase by adding about 0.1 to about 0.5 parts by weight of a second thickener previously dispersed to the homogenized film-former phase; (4) manufacturing a neutralized thickener phase by adding about 0.08 to about 0.4 parts by weight of a neutralizing agent to the homogenized thickener phase to thus increase viscosity, and performing cooling to about 35° C.; (5) manufacturing a secondarily homogenized film-former phase by adding about 1 to about 10 parts by weight of polyvinyl pyrrolidone to about 5 to about 15 parts by weight of alcohol, performing homogenization, and adding a resultant homogenized material to the neutralized thickener phase; (6) manufacturing a conditioning phase by adding about 1 to about 5 parts by weight of silicone to the secondarily homogenized film-former phase; and (7) adding about 0.01 to about 0.5 parts by weight of pearl or powder particles to the conditioning phase.

When the cosmetic composition for peel-off-type packs further including an additive is manufactured, during step (1), about 0.01 to about 0.1 parts by weight of the additive may be further mixed with the first thickener.

When the cosmetic composition for peel-off-type packs further including a preservative or a fragrance is manufactured, after step (5), about 0.1 to about 1 part by weight of the preservative or about 0.1 to about 1 part by weight of the fragrance may be added to about 1 to about 10 parts by weight of the alcohol and may then be homogenized, followed by step (6).

A cosmetic composition for peel-off-type packs of the present invention is useful to remove keratinized stratum corneum and includes two kinds of thickeners so that the viscosity thereof is controlled and pearl or powder particles are stabilized in a formulation to thus impart a sophisticated and differentiated appearance. The content of an alcohol ingredient therein is controlled to accelerate drying, which maximizes the lifting effect. Silicone, imparting a feeling of conditioning, is introduced into polyvinyl alcohol and polyvinyl pyrrolidone, which are film formers, thus minimizing skin irritation upon peeling off.

DETAILED DESCRIPTION

The present invention will be described more fully hereinafter with reference to the accompanying drawings, in which embodiments of the present invention are shown so as to be easily understood by those skilled in the art. However, the present invention may be embodied in many different forms, but is not limited to the embodiments described herein. In order to clearly illustrate the present invention, parts not related to the description are omitted in the drawings, and similar reference numerals are used for similar components throughout the specification.

It is to be understood that the terms or words used in the specification and claims of the present invention are not to be construed in a conventional or dictionary sense, and that the inventors can properly define the concept of a term to describe their invention in the best possible way. Accordingly, the present invention should be construed as having a meaning and concept consistent with the technical idea of the present invention.

In the specification of the present invention, when any portion "includes" any component, this means that the portion does not exclude other components, but may further include other components unless otherwise stated.

In the specification of the present invention, "A and/or B" means A or B or A and B.

Hereinafter, the present invention has been specifically described with reference to the accompanying drawings, but the present invention is not limited thereto.

The present invention provides a cosmetic composition for peel-off-type packs, including pearl or powder particles, a first thickener, polyvinyl alcohol, a second thickener, a neutralizing agent, alcohol, polyvinyl pyrrolidone, and silicone.

The cosmetic composition for peel-off-type packs may include about 0.01 to about 0.5 parts by weight of pearl or powder particles, about 0.1 to about 0.5 parts by weight of the first thickener, about 5 to about 20 parts by weight of polyvinyl alcohol, about 0.1 to about 0.5 parts by weight of the second thickener, about 0.08 to about 0.4 parts by weight of the neutralizing agent, about 6 to about 25 parts by weight of alcohol, about 1 to about 10 parts by weight of polyvinyl pyrrolidone, and about 1 to about 5 parts by weight of silicone.

In an embodiment of the present invention, it is preferable to use polyvinyl alcohol and polyvinyl pyrrolidone mixed in appropriate amounts as a former for films capable of being peeled off. In the case where only polyvinyl alcohol is used, the skin is greatly irritated when it is peeled off, and the film may be hardened and thus break. In the case where only polyvinyl pyrrolidone is used, a film capable of being peeled off is not formed.

Therefore, it is preferable that about 5 to about 20 parts by weight of polyvinyl alcohol and about 1 to about 10 parts by weight of polyvinyl pyrrolidone be contained based on 100 parts by weight of the cosmetic composition for peel-off-type packs.

The cosmetic composition for peel-off-type packs may further include purified water in order to improve mixing workability. The purified water may be deionized water or distilled water, and may be included in an amount of about 5 to about 100 parts by weight or about 8 to about 75 parts by weight in the cosmetic composition for peel-off-type packs. The purified water may be used for homogenizing the first thickener, the second thickener, and the neutralizing agent before mixing, so that the mixing workability is improved.

The cosmetic composition for peel-off-type packs may further include about 0.01 to about 0.1 parts by weight of an additive, but may not be limited thereto. The additive may be homogenized in advance in the purified water to be mixed.

The additive may include a substance for imparting a function, for example, a skin nutrient, a skin elasticity improving agent, an anti-oxidant, an anti-irritant, or a skin sedative. Particularly, dipotassium glycyrrhizate, having skin-barrier-strengthening and anti-irritation effects, and/or allantoin, having skin-soothing and alleviating effects, may be included as the additive, without being limited thereto.

The cosmetic composition for peel-off-type packs may further include about 0.1 to about 1 part by weight of a fragrance, but may not be limited thereto. The fragrance may be homogenized in advance in alcohol to be mixed.

It is preferable that the alcohol be monovalent or divalent alcohol rather than polyol. For example, the alcohol may include one or more selected from the group consisting of ethanol, denatured ethanol, propylene glycol, and butylene glycol.

The alcohol can be absorbed into the skin and volatilized, thus contributing to shortening of the drying time of the cosmetic composition for peel-off-type packs.

In the embodiment of the present invention, the thickener is used for two purposes. The first thickener serves to control the viscosity of the cosmetic composition for peel-off-type packs, thus preventing the cosmetic composition from flowing down even when a thick film is formed during application on the skin. The second thickener contributes to the stabilization of the pearl or powder particles contained in the cosmetic composition for peel-off-type packs, thereby preventing the pearl or powder particles from aggregating or separating in the formulation. Preferably, each of the first thickener and the second thickener is used in an amount of about 0.1 to about 0.5 parts by weight. When the first thickener is included in an amount of less than 0.1 parts by weight in the cosmetic composition for peel-off-type packs, since the viscosity of the formulation is very low, the cosmetic composition continuously flows down during application on the skin, making it difficult to use. When the first thickener is included in an amount of more than 0.5 parts by weight in the cosmetic composition for peel-off-type packs, since the viscosity of the formulation is very high, it is difficult to perform uniform application, which is not desirable. Further, when the second thickener is included in an amount of less than 0.1 parts by weight in the cosmetic composition for peel-off-type packs, the pearl or powder particles are not stabilized, and thus precipitate over time. When the second thickener is included in an amount of more than 0.5 parts by weight in the cosmetic composition for peel-off-type packs, since dispersion in the formulation is not easy, homogenization cannot be achieved, which is not preferable.

The first thickener may include a material selected from the group consisting of natural polymers such as gum arabic, carrageenan, galactan, agar, guar gum, pectin, mannan, wheat starch, rice starch, corn starch, potato starch, xanthan gum, albumin, collagen, and gelatin; semi-synthetic polymers such as ethyl cellulose, carboxymethyl cellulose or salts thereof, carboxymethyl ethyl cellulose or salts thereof, crystalline cellulose, hydroxyethyl cellulose, hydroxymethyl cellulose, and methyl hydroxypropyl cellulose; and synthetic polymers such as carboxyvinyl polymers, sodium polyacrylate, polyvinyl alcohol, and acrylate/alkyl acrylate crosspolymers. For example, the first thickener is preferably cellulose gum (a sodium salt of carboxymethyl ethyl cellulose), but may not be limited thereto.

The second thickener may include a material selected from the group consisting of natural polymers such as gum arabic, carrageenan, galactan, agar, guar gum, pectin, mannan, wheat starch, rice starch, corn starch, potato starch, xanthan gum, albumin, collagen, and gelatin; semi-synthetic polymers such as ethyl cellulose, carboxymethyl cellulose or salts thereof, carboxymethyl ethyl cellulose or salts thereof, crystalline cellulose, hydroxyethyl cellulose, hydroxymethyl cellulose, and methyl hydroxypropyl cellulose; and synthetic polymers such as carboxyvinyl polymers, sodium polyacrylate, polyvinyl alcohol, and acrylate/alkyl acrylate crosspolymers. For example, the second thickener is preferably a carboxyvinyl polymer (abbreviated as "carbomer"), but may not be limited thereto.

The carboxyvinyl polymer is a polymer compound exhibiting acidity, and the pH needs to be adjusted using a neutralizing agent in order to reduce skin irritation. Accordingly, about 0.08 to about 0.4 parts by weight of the neutralizing agent is used in the present invention. Tromethamine may be used as the neutralizing agent, without limitation thereto.

Silicone is a skin-softening agent or a conditioning agent, and is used for the purpose of imparting a feeling of moistness in use after peeling off and facilitating removal of the dried film, thereby alleviating skin irritation.

As the silicone used to easily remove the dried film, for example, one or more selected from the group consisting of decamethylcyclopentasiloxane, dimethicone, methyl polysiloxane, pentasiloxane, hexasiloxane, and phenyl dimethicone may be used. When the silicone is included in an amount of less than 1 part by weight in the cosmetic composition for peel-off-type packs, a user cannot feel moistness in use upon peeling off, and the dried film may be hardened to thus cause skin irritation when the dried film is peeled off. When the content of silicone is included in an amount of more than 5 parts by weight in the cosmetic composition for peel-off-type packs, the drying speed may be very slow and the stability of the formulation may be reduced.

The pearl particles may include a pearlizing agent capable of imparting a differentiated appearance. For example, gold pearl particles, that is, mica/red iron oxide/titanium dioxide/tin oxide may be used, without limitation thereto.

The powder particles may be micro-sized powder particles having a size of several to several hundreds of micrometers, and may include fine solid particles, which are not soluble in purified water or alcohol, without limitation thereto.

In addition, the present invention provides a method of manufacturing a cosmetic composition for peel-off-type packs, and the manufacturing process thereof is as follows:

(1) Manufacture of Homogenized Water-Phase Part

A thickener is slowly added to purified water, and agitation is performed at a temperature of about 70 to about 90° C. using a homo mixer provided with paddles of about 10 to about 40 rpm so that a rotation speed is about 2,000 to about 3,000 rpm, thus manufacturing a homogenized water-phase part. When the homo mixer provided with the paddles is used, the thickener is easily dispersed.

(2) Manufacture of Primarily Homogenized Film-Former Phase

Polyvinyl alcohol is added to the homogenized water-phase part that is manufactured, and agitation is performed in a typical vacuum homo agitation tank at a temperature of about 70 to about 90° C. using a homo mixer provided with paddles of about 10 to about 40 rpm so that a rotation speed is about 2,500 to about 3,500 rpm, thus manufacturing a primarily homogenized film-former phase.

(3) Manufacture of Homogenized Thickener Phase

The thickener that has been dissolved in separate purified water is added to the primarily homogenized film-former phase that is manufactured, and agitation is performed at a temperature of about 70 to about 90° C. using a homo mixer provided with paddles of about 10 to about 40 rpm so that the rotation speed is about 2,500 to about 3,500 rpm, thus manufacturing a homogenized thickener phase.

(4) Manufacture of Neutralized Thickener Phase

A neutralizing agent is added to the homogenized thickener phase that is manufactured, and agitation is performed at a temperature of about 70 to about 90° C. using a homo mixer provided with paddles of about 10 to about 40 rpm so that a rotation speed is about 2,500 to about 3,500 rpm, which neutralizes the thickener to thus increase the viscosity thereof, whereby the neutralized thickener phase is manufactured. Subsequently, the temperature of the neutralized thickener phase is decreased to about 25 to about 40° C.

(5) Manufacture of Secondarily Homogenized Film-Former Phase

Polyvinylpyrrolidone is added to alcohol, and agitation is performed using a homo mixer provided with paddles of about 10 to about 40 rpm so that a rotation speed is about 2,500 to about 3,500 rpm, thus manufacturing a secondarily homogenized film-former phase.

(6) Manufacture of Conditioning Phase

Silicone is added to the secondarily homogenized film-former phase that is manufactured while agitation is maintained using a homo mixer provided with paddles of about 10 to about 40 rpm so that a rotation speed is about 2,500 to about 3,500 rpm, thus manufacturing a conditioning phase for controlling a feeling of use.

(7) Addition of Pearl or Powder Particles

Pearl or powder particles are finally added to the manufactured conditioning phase at a temperature of 35° C. while agitation is maintained using a homo mixer provided with paddles of about 10 to about 40 rpm so that a rotation speed is about 2,500 to about 3,500 rpm, thus manufacturing a cosmetic composition for peel-off-type packs.

When the cosmetic composition for peel-off-type packs further including an additive capable of imparting various functions is manufactured, during step (1), about 0.01 to about 0.1 parts by weight of the additive may be further mixed with the first thickener, thus manufacturing the homogenized water-phase part.

When the cosmetic composition for peel-off-type packs further including a preservative or a fragrance is manufactured, after step (5), about 0.1 to about 1 part by weight of the preservative or about 0.1 to about 1 part by weight of the fragrance may be added to about 1 to about 10 parts by weight of alcohol and then homogenized, followed by step (6).

The finally manufactured cosmetic composition for peel-off-type packs is preferably stored at room temperature or lower.

With respect to the method of manufacturing the cosmetic composition for peel-off-type packs, portions that overlap the detailed description of the cosmetic composition for peel-off-type packs are omitted. However, even if the content that describes the method of manufacturing the cosmetic composition for peel-off-type packs of the present invention is omitted in the method of manufacturing the cosmetic composition for peel-off-type packs of the present invention, the content may be applied equally.

The cosmetic composition for peel-off-type packs according to an embodiment of the present invention may be manufactured for commercial use according to a typically known method.

In the cosmetic composition for peel-off-type packs manufactured according to the embodiment of the present invention, an appropriate thickener may be applied, so that solid particles such as pearl or powder are stabilized in a formulation to thus impart a sophisticated and differentiated appearance. In addition, in the cosmetic composition for peel-off-type packs, the combination amount of polyvinyl alcohol and polyvinyl pyrrolidone and the content of silicone may be controlled, thus minimizing irritation. Accordingly, when the cosmetic composition is applied on the skin, since sebum or various kinds of waste materials in keratinized stratum corneum and pores are adsorbed on the dried film to thus be removed while the film is peeled off, immediate waste removal as well as nutrition supply is feasible. Further, an alcohol ingredient may be suitably mixed to accelerate drying, which maximizes the lifting effect.

Hereinafter, the present invention will be described in more detail with reference to Examples. However, the following Examples are given for the purpose of helping understanding of the present invention, but the present invention is not limited to the following Examples.

MANUFACTURE OF EXAMPLES AND COMPARATIVE EXAMPLES

Manufacture of Cosmetic Composition for Peel-Off-Type Packs

According to the components and amounts of Examples and Comparative Examples 1 to 10 shown in the following Tables 1 and 2, a cosmetic composition for peel-off-type packs that included stabilized pearl and micrometer-sized powder particles, had a rapid drying speed, and caused minimal irritation was manufactured. Denatured ethyl alcohol was used as the alcohol.

TABLE 1

| Classification | Component | Example 1 | Example 2 | Comparative Example 1 | Comparative Example 2 | Comparative Example 3 | Comparative Example 4 |
|---|---|---|---|---|---|---|---|
| Water-phase part | Purified water | 70.52 | 22.4 | 39.5 | 38.75 | 51.14 | 24.14 |
| | Dipotassium glycyrrhizate | 0.05 | 0.05 | 0.05 | 0.05 | 0.05 | 0.05 |
| | Allantoin | 0.05 | 0.05 | 0.05 | 0.05 | 0.05 | 0.05 |
| | Cellulose gum | 0.1 | 0.5 | 0.05 | 0.8 | 0.3 | 0.3 |
| Main film former | Polyvinyl alcohol | 5.0 | 20.0 | 15 | 15 | 3 | 30 |
| Second thickener | Purified water | 10 | 10 | 10 | 10 | 10 | 10 |
| | Carbomer | 0.1 | 0.5 | 0.2 | 0.2 | 0.2 | 0.2 |
| Neutralizing agent | Purified water | 5 | 5 | 5 | 5 | 5 | 5 |
| | Tromethamine | 0.08 | 0.4 | 0.05 | 0.05 | 0.16 | 0.16 |
| Auxiliary film former | Alcohol | 5 | 15 | 13 | 13 | 13 | 13 |
| | Polyvinyl pyrrolidone | 1 | 10 | 5 | 5 | 5 | 5 |
| Preservative and flavoring agent | Alcohol | 1 | 10 | 8 | 8 | 8 | 8 |
| | Preservative | 0.5 | 0.5 | 0.5 | 0.5 | 0.5 | 0.5 |
| | Fragrance | 0.5 | 0.5 | 0.5 | 0.5 | 0.5 | 0.5 |
| Silicone | Dimethicone | 1 | 5 | 3 | 3 | 3 | 3 |
| Gold pearl particles | Mica/red iron oxide/titanium dioxide/tin oxide | 0.1 | 0.1 | 0.1 | 0.1 | 0.1 | 0.1 |

TABLE 2

| Classification | Component | Comparative Example 5 | Comparative Example 6 | Comparative Example 7 | Comparative Example 8 | Comparative Example 9 | Comparative Example |
|---|---|---|---|---|---|---|---|
| Water-phase part | Purified water | 39.41 | 38.06 | 63.94 | 15.14 | 66.84 | 8.14 |
| | Dipotassium glycyrrhizate | 0.05 | 0.05 | 0.05 | 0.05 | 0.05 | 0.05 |
| | Allantoin | 0.05 | 0.05 | 0.05 | 0.05 | 0.05 | 0.05 |
| | Cellulose gum | 0.3 | 0.3 | 0.3 | 0.3 | 0.3 | 0.3 |
| Main film former | Polyvinyl alcohol | 15 | 15 | 15 | 15 | 15 | 15 |
| Second thickener | Purified water | 10 | 10 | 10 | 10 | 10 | 10 |
| | Carbomer | 0.05 | 0.8 | 0.2 | 0.2 | 0.2 | 0.2 |
| Neutralizing agent | Purified water | 5 | 5 | 5 | 5 | 5 | 5 |
| | Tromethamine | 0.04 | 0.64 | 0.16 | 0.16 | 0.16 | 0.16 |
| Auxiliary film former | Alcohol | 13 | 13 | 1 | 20 | 1 | 20 |
| | Polyvinyl pyrrolidone | 5 | 5 | 0.1 | 15 | 0.1 | 15 |
| Preservative and flavoring agent | Alcohol | 8 | 8 | 0.1 | 15 | 0.1 | 15 |
| | Preservative | 0.5 | 0.5 | 0.5 | 0.5 | 0.5 | 0.5 |
| | Fragrance | 0.5 | 0.5 | 0.5 | 0.5 | 0.5 | 0.5 |
| Silicone | Dimethicone | 3 | 3 | 3 | 3 | 0.1 | 10 |
| Gold pearl particles | Mica/red iron oxide/titanium dioxide/tin oxide | 0.1 | 0.1 | 0.1 | 0.1 | 0.1 | 0.1 |

<Mixing Process>

Purified water was added to a vacuum emulsification agitation tank capable of controlling temperatures and performing agitation and homo processing, heating was performed to 70 to 90° C., and an additive and a thickener were added thereto to thus homogenize a water-phase part. A main film former was added thereto while agitation was continually performed using a paddle mixer and a homo mixer of 10 to 40 rpm so that a rotation speed is 2,500 to 3,500 rpm. A second thickener, which had been dissolved separately in purified water, was added thereto while the temperature and the agitation speed were maintained, thus performing neutralization. When the neutralization was finished, cooling was performed to 35° C., and an auxiliary film former and a preservative/flavoring agent, which had been dissolved in separate alcohol, were added thereto and homogenized.

Silicone was added, and gold pearl particles were added at 35° C., thus manufacturing a cosmetic composition for peel-off-type packs.

Experimental Example 1: Characteristics and Physical Properties of Examples and Comparative Examples 1 to 10

The cosmetic compositions for peel-off-type packs manufactured in the Examples were obtained by setting a mixing ratio so that gold pearl particles were stabilized, a drying speed was fast, and a feeling of use and characteristics of minimal irritation were secured. It was confirmed that the gold pearl particles stably floated even under a severe condition of 50° C. or more and were stable over a long period of time without agglomeration or separation in the formulation.

However, when the content of the first thickener (cellulose gum) was less than 0.1 parts by weight, as in Comparative Example 1, since the viscosity of the formulation was low, the cosmetic composition continuously flowed down during application on the skin, making it difficult to use. When the first thickener was applied so that the content of the first thickener was more than 0.5 parts by weight, as in Comparative Example 2, since the viscosity of the formulation was very high, it was difficult to perform uniform application, and it was not easy to use.

When polyvinyl alcohol was used in an amount of less than 5 parts by weight, as in Comparative Example 3, it was confirmed that the tensile strength of the film upon peeling off was so poor that it could not effectively absorb waste materials. When polyvinyl alcohol was used in an amount of more than 20 parts by weight, as in Comparative Example 4, since a user experienced strong irritation and the viscosity of the formulation was very high, it was not easy to use.

When the content of carbomer was less than 0.1 parts by weight, as in Comparative Example 5, the gold pearl particles did not stably float and the stability of the formulation was deteriorated as they descended over time. When the content of carbomer was more than 0.5 parts by weight, as in Comparative Example 6, since dispersion of the gold pearl particles in the formulation was not easy, the phase was not homogenized.

When the total content of alcohol was less than 6 parts by weight, as in Comparative Example 7, a drying speed was very slow, which was not preferable. When the content of polyvinyl pyrrolidone was less than 1 part by weight, the film was hardened, making it difficult to use. In addition, when the total content of alcohol was more than 25 parts by weight, as in Comparative Example 8, irritation and eye stinging occurred when the cosmetic composition was applied on the skin. When the content of polyvinyl pyrrolidone was more than 10 parts by weight, the viscosity of the formulation was too high to be easily used.

When the content of dimethicone was less than 1 part by weight, as in Comparative Example 9, a user did not have a feeling of moistness in use upon peeling off, and the dried film was hardened to thus cause skin irritation when the dried film was peeled off. When the content of dimethicone was more than 5 parts by weight, as in Comparative Example 10, the drying speed was very slow, thus reducing the stability of the formulation.

Experimental Example 2: Skin Application Experiment

In order to confirm the lifting effect and the keratinous-waste-removal effect of the cosmetic compositions for peel-off-type packs manufactured in the Examples, 21 women of 20 to 59 years old were selected as subjects (mean age: 36.48 years). After cleansing, the cosmetic composition for peel-off-type packs manufactured in the Example was abundantly spread on the skin of each subject. When the cosmetic composition was completely dried after 20 to 30 minutes, the dried film was peeled off. The above-described procedure was repeated once a day for 7 days. Before use, immediately after one use, and 7 days after use, the keratin removal effect and the skin elasticity change at the edge of the eye and at the edge of the mouth of each subject were observed.

Figure 1:
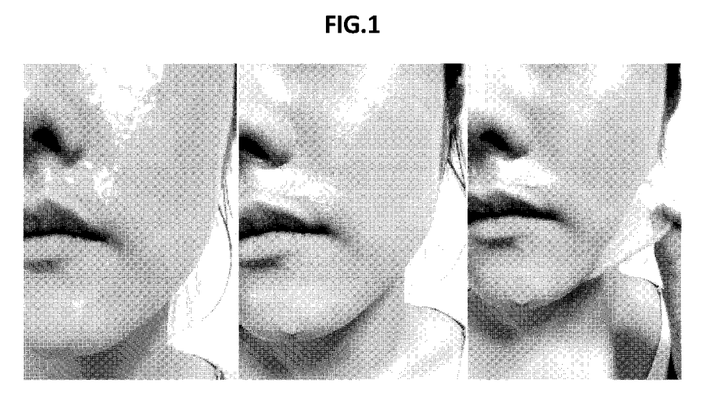
FIG. 1 is a picture obtained by photographing a cosmetic composition for peel-off-type packs which is manufactured according to an Example of the present invention and which is applied on the skin.

With respect thereto, the state of the composition was photographed at the time of application and until a peeling-off process 15 minutes after application, and is shown in FIG. 1.

As shown in FIG. 1 [left: immediately after application, middle: dried, and right: during peeling off], the cosmetic compositions for peel-off-type packs manufactured in the Examples did not flow down, but adhered to the skin even though they were applied on the skin in a sufficiently large amount. Further, the cosmetic compositions dried less than 15 minutes after application and were easily peeled off 15 minutes after application. That is, it can be seen that the cosmetic compositions for peel-off-type packs manufactured in the Examples are rapidly dried.

(1) Effect of Removing Keratinous Waste Materials

In order to confirm the effect of removing keratinous waste materials by the cosmetic compositions for peel-off-type packs manufactured in the Examples, the keratin percentage values before use, immediately after use (once), and one week after use were measured and are shown in the following Table 3. The keratin measurement was performed in P & K Skin Clinical Research Center Co., Ltd., and the cheek skin near the facial cheekbones was measured using a VISIOSCAN VC98 (Courage+Khazaka electronic GmbH, Germany). For the measurement, after keratin was collected using a special film (Corneofix), images were photographed using VISIOSCAN VC98 and were analyzed, and a D.I. (desquamation index, %) was used as skin keratin evaluation data.

$$D.I = \frac{2.4 + \sum_{n=1}^{5} Tn * (n-1)}{6}$$

A: Percent area covered by corneocytes
Tn: Percentage of corneocytes in relation to thickness
n: Thickness level (thickness level=1-5)

TABLE 3

| Classification | % |
| --- | --- |
| Before use | 19.26 ± 2.17 |
| Immediately after use | 12.56 ± 3.58 |
| 1 week after use | 15.62 ± 3.23 |

$P < 0.05$ by repeated measures ANOVA, post hoc Bonferroni correction

As shown in Table 3, as the results of the normality test performed using repeated ANOVA, which is a parametric method and the posterior test performed using a Bonferroni correction, the measurement values of the keratin were statistically significantly reduced, i.e. p was less than 0.05 both immediately after use and one week after use, compared to the values before use.

(2) Lifting Effect

Figure 2A:
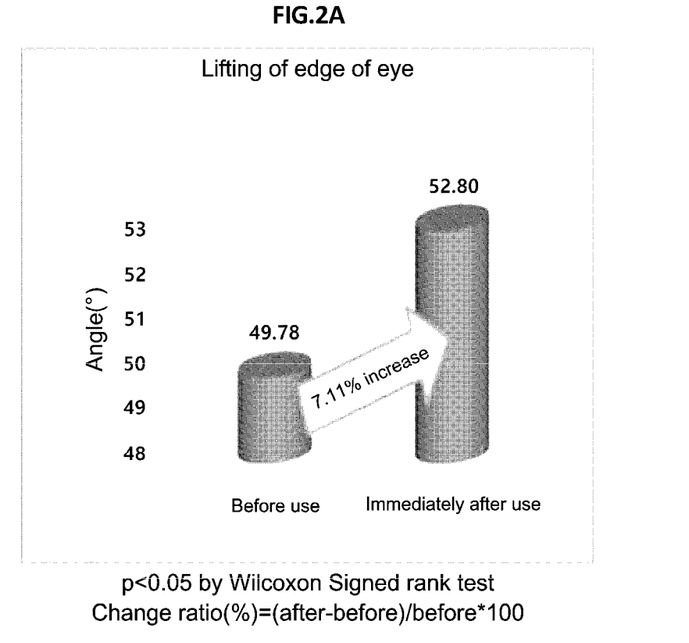
FIGS. 2A and 2B are graphs showing a lifting effect according to the cosmetic composition for peel-off-type packs manufactured in the Example of the present invention.
Figure 2B:
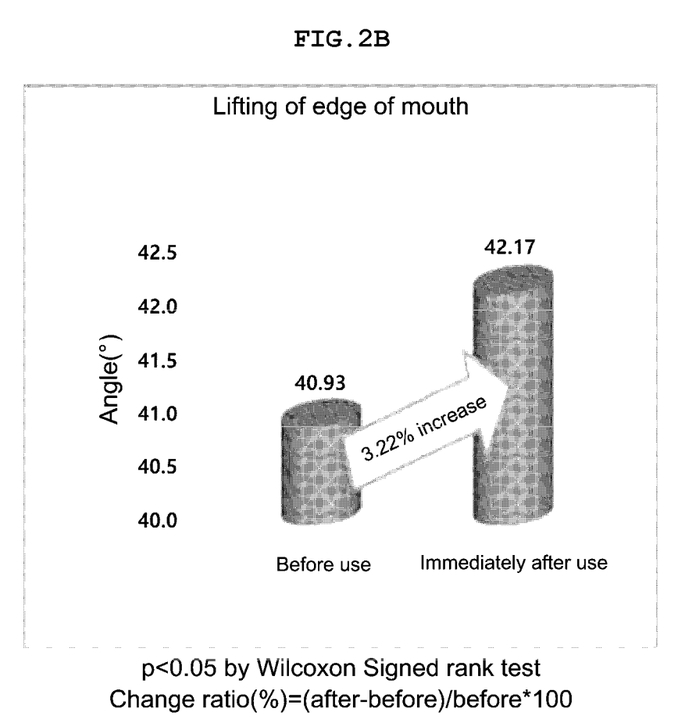

A human-body application test for the lifting (the edge of the eye and the edge of the mouth) of 21 subjects was requested to P & K Skin Clinical Research Center Co., Ltd., and the results thereof are shown in FIGS. 2A and 2B. In the images photographed using an F-ray, which is a device for expressing the shape of the skin in contour lines, the edge of the eye and the edge of the mouth were analyzed using an Image-Pro® plus. For the mechanical evaluation, the subjects were stabilized in a waiting room under constant-temperature and constant-humidity conditions of a temperature of 20 to 25° C. and 40 to 60% humidity for 30 minutes to thus adapt the temperature and the humidity of the skin surface to the environment of the measurement space. Water intake was restricted while they were stabilized. For objective measurement, the same researcher measured the same area for each measurement.

The lifting of the edge of the eye was evaluated by measuring the angle (°) between a line drawn to be parallel to the tip of the edge of the eye and a line extending from the end point of the edge of the eye. Similarly, the lifting of the edge of the mouth was evaluated by measuring the angle between a line drawn to be parallel to the tip of the edge of the mouth and a line drawn downwards.

Referring to FIGS. 2A and 2B, the lifting effect of the cosmetic compositions for peel-off-type packs manufactured in the Examples was confirmed immediately after use, and the measurement values of lifting of the edge of the eye before use and immediately after use were 49.78±12.97° and 52.80±12.24°. An angular increase of 7.11% was confirmed immediately after one use. The measurement values of lifting of the edge of the mouth before use and immediately after use were 40.93±9.12° and 42.17±9.09°. An angular increase of 3.22% was confirmed immediately after one use. As the result of the normality test performed using a Wilcoxon signed rank test, which is a nonparametric method, the measurement values of the lifting of the edge of the eye and the edge of the mouth were statistically significantly increased, so that p was less than 0.05 immediately after use, compared to the values before use.

Taking the results of the Examples and the Comparative Examples into consideration, it can be found that when the cosmetic composition for peel-off-type packs which includes stabilized pearl or micro-sized powder particles, which has a rapid drying speed, and which causes minimal irritation is manufactured, the content of the second thickener is very important for stabilizing the gold pearl or micro-sized powder particles, and it can also be found that appropriate alcohol content is very important for improving the drying speed. In addition, by using the above-described method, it is possible to stabilize the gold pearl or micro-sized powder particles in a formulation to thus impart a sophisticated and differentiated appearance. Further, it is possible to maximize the lifting effect according to the improvement of the drying speed, and it is also possible to control the combination of polyvinyl alcohol and polyvinyl pyrrolidone film formers and the content of silicone, thus minimizing irritation.

It will be apparent to those skilled in the art that various modifications and variations can be made in the present invention without departing from the spirit or scope of the present invention. Therefore, it should be understood that the above-described embodiments are illustrative in all aspects and not restrictive. For example, each component described as a single entity may be embodied in a distributed state, and components described as being distributed may be embodied in a combined form.

The scope of the present invention is defined by the appended claims rather than the detailed description, and all changes or modifications derived from the meaning and scope of the claims and their equivalents are to be construed as being included within the scope of the present invention.

What is claimed is:

1. A cosmetic composition for a peel-off-type pack, the composition comprising:
   pearl or powder particles;
   a first thickener comprising a cellulose gum;
   a second thickener comprising carboxyvinyl polymers;
   a film former consisting of polyvinyl alcohol and polyvinyl pyrrolidone;
   silicone selected from the group consisting of decamethylcyclopentasiloxane, dimethicone, methyl polysiloxane, pentasiloxane, hexasiloxane, phenyl dimethicone, and a combination thereof; and
   an alcohol,
   wherein the cosmetic composition includes:
   0.01 to 0.5% by weight of the pearl or powder particles, based on the total weight of the cosmetic composition;
   0.1 to 0.5% by weight of the cellulose gum, based on the total weight of the cosmetic composition;
   0.1 to 0.5% by weight of the carboxyvinyl polymers, based on the total weight of the cosmetic composition;
   5 to 20% by weight of the polyvinyl alcohol, based on the total weight of the cosmetic composition;
   1 to 10% by weight of the polyvinyl pyrrolidone, based on the total weight of the cosmetic composition;
   1 to 5% by weight of the silicone, based on the total weight of the cosmetic composition; and
   6 to 25% by weight of the alcohol, based on the total weight of the cosmetic composition.

2. The cosmetic composition of claim 1, wherein the silicone includes dimethicone.

* * * * *